United States Patent [19]

De Barbieri

[11] 4,216,208
[45] Aug. 5, 1980

[54] N-ACYL DERIVATIVES OF GLUCOSAMINES HAVING ANTITUMOR CHEMOTHERAPEUTIC ACTIVITY

[75] Inventor: Augusto De Barbieri, Milan, Italy
[73] Assignee: Proter S.p.A., Milan, Italy
[21] Appl. No.: 929,237
[22] Filed: Jul. 31, 1978
[51] Int. Cl.$^2$ .................. A61K 37/00; C07C 103/52; A61K 31/70
[52] U.S. Cl. .................. 424/177; 260/112.5 R; 424/180; 536/53
[58] Field of Search .................. 536/53; 260/112.5 R; 424/177

[56] References Cited

PUBLICATIONS

Siggins et al., J.A.C.S. 1966, pp. 971–973.
Adam et al., Biochem. and Biophys. Res. Commun. 72, 1976, pp. 339–346.

Primary Examiner—Delbert R. Phillips
Attorney, Agent, or Firm—Fisher, Christen & Sabol

[57] ABSTRACT

N-Acyl derivatives of glucosamines made by linking an amino acid or oligopeptide having a m-di(2-chloroethyl)amino-L-phenylalanyl group, to the amino group of the glucosamines by a peptide bond, are endowed with strong anti-tumor action against transplanted neoplasma in animal. The compounds according to the present invention are of the general formula (I):

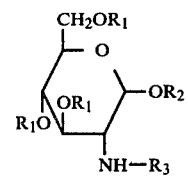

where
$R_1$ is a hydrogen atom or an acetyl group,
$R_2$ is a hydrogen atom, an acetyl group, aliphatic ($C_1$–$C_6$) group or a benzyl group
and $R_3$ is m-di(2-chloroethyl) amino-L-phenylalanine, or L- methionyl -m-di(2-chloroethyl) amino-L-phenylalanyl-p-fluoro-L-phenylalanine, or p-fluoro-L-phenylalanyl-m-di (2-chloroethyl) amino-L-phenylalanyl-L-proline, or m-di (2-chloroethyl) amino-L-phenylalanyl-L-methionyl-p-fluoro-L-phenylalanine.

The antineoplasmic activity of the compounds of the present invention is not affected in the gastrointestinal tract and hence they can be effectively administered orally.

16 Claims, No Drawings

N-ACYL DERIVATIVES OF GLUCOSAMINES HAVING ANTITUMOR CHEMOTHERAPEUTIC ACTIVITY

Background of the Invention

The present invention relates to acyl derivatives of glucosamines with amino acids or synthetic peptides, endowed with antitumor chemotherapeutic activity against transplanted tumors in animals, to pharmaceutical compositions containing said derivatives, to processes for their preparation, and to processes for their chemotherapeutic administration.

Antitumor chemotherapy has been and still is an object of intensive research. Certain positive results have undoubtedly been achieved, especially by means of polychemotherapy realized by associating different active substances according to carefully developed protocols. However, the ideal therapy has not yet been found. The need to find new active substances has been particularly emphasized. All the foregoing justifies continuous research directed towards preparing new chemotherapeutic compounds active against tumors. There are already known peptides having antitumor activity, consisting of both normal and antimetabolic amino acids, coupled by means of a peptide bond. Such peptides have for years been in therapeutic use with favorable results both in monochemotherapy and in polychemotherapy. However, their adoption encounters obstacles of various kinds, which are connected, among other things, with the impossibility of being administered by the oral route because of inactivation of the said peptides in the gastrointestinal tract.

It has now surprisingly been found that the said difficulty is overcome by a series of new compounds possessing antitumor activity against transplanted tumors in animals, characterized by the presence of a molecule of a glucosamine. The glucosamine is used as a carrier of an anti-tumor-active compound wherein the anti-tumor-active molecule is bound to the $-NH_2$ group of the glucosamine, said tumors being transplanted into animals. For example, the amino group of the glucosamine is acylated by the carboxyl group of an antitumor amino acid or peptide. The resulting acyl derivatives of the glucosamines of the present invention are not inactivated in the gastrointestinal tract and are useful in controlling transplanted neoplasms in animals.

SUMMARY OF THE INVENTION

It is an object of the present invention to provide novel compounds which are effective in controlling transplanted neoplasms in animals.

It is another object of the present invention to provide novel compounds which can be administered orally without undergoing deactivation in the gastrointestinal tract.

It is a further object of the present invention to provide a process for preparing the N-acyl derivatives of glucosamines of the present invention.

It is still another object of the present invention to provide pharmaceutical compositions which are effective in controlling transplanted neoplasms in animals and which contain at least one of the novel compounds of the present invention as an active ingredient.

These and other objects of the present invention are accomplished by condensing a D-glucosamine with an amino acid or with a peptide to form via peptide linkage, a compound of the general formula (I):

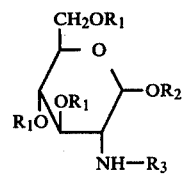

where
$R_1$ is a hydrogen atom or an acetyl group,
$R_2$ is a hydrogen atom, an acetyl group, aliphatic ($C_1$-$C_6$) group or a benzyl group
and $R_3$ is m-di(2-chloroethyl)amino-L-phenylalanine, or L-methionyl-m-di(2-chloroethyl)amino-L-phenylalanyl-p-fluoro-L-phenylalanine, or p-fluoro-L-phenylalanyl-m-di(2-chloroethyl)amino-L-phenylalanyl-L-proline, or m-di(2-chloroethyl)amino-L-phenylalanyl-L-methionyl-p-fluoro-L-phenylalanine.

DETAILED DESCRIPTION OF THE INVENTION

The compounds of the present invention have the general formula (I):

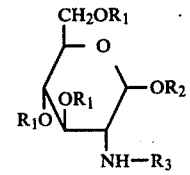

where:
$R_1 = -H$; $-COCH_3$ (an acetyl group),
$R_2 = -H$; $-COCH_3$; a $C_1$-$C_6$ alkyl group; or a benzyl group,

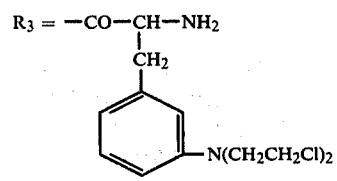

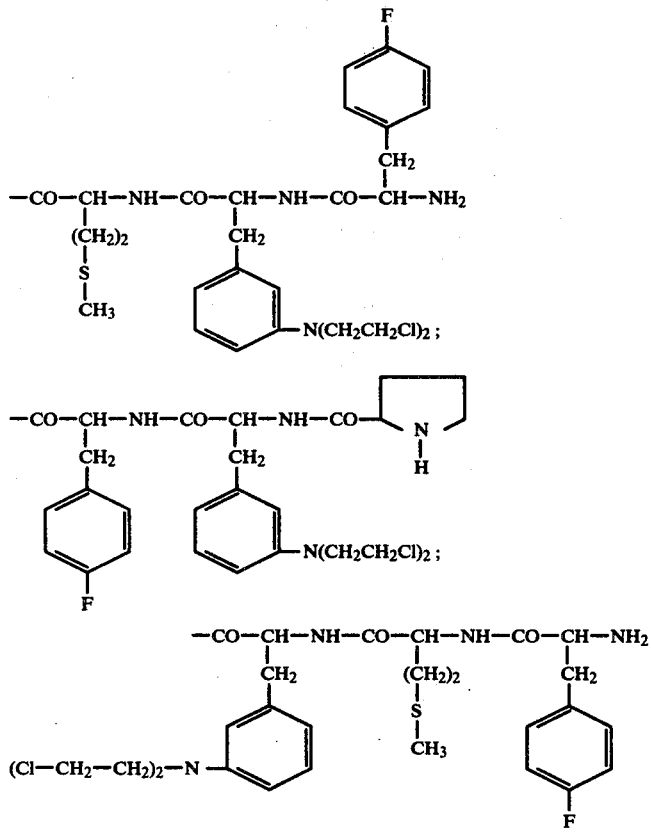

The salts of the compounds of formula I with organic or inorganic acids which are physiologically tolerated also exhibit antitumor activity and are contemplated by the present invention. The preferred inorganic acid for forming the salts of the present invention is hydrochloric acid. Acetic acid is the preferred organic acid for forming the salts of the present invention.

In the above general formula I, exemplary of the hydrocarbon groups that are represented by $R_2$ are the $C_1$–$C_6$ alkyl groups (for example, the methyl, ethyl, isopropyl, n-butyl and 2-methyl-pentyl groups) and the benzyl group. However, other alkyl groups or aralkyl groups, or monovalent hydrocarbon groups which result in compounds which are chemotherapeutically active against neoplasms by the oral route are also covered by $R_2$. The preferred monovalent hydrocarbon groups represented by $R_2$ are the $C_1$ to $C_6$ alkyl groups (—$CH_3$, —$C_2H_5$, —$C_3H_7$, —$C_4H_9$, —$C_5H_{11}$, —$C_6H_{13}$) and the benzyl group,

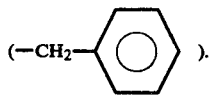

The $C_1$ to $C_6$ alkyl groups are the most preferred groups for the $R_2$ position.

In other words, the novel compounds are constituted of a molecule of a glucosamine (actually, a mixture of the two α and β anomers the latter in general being prevalent) of the general formula II:

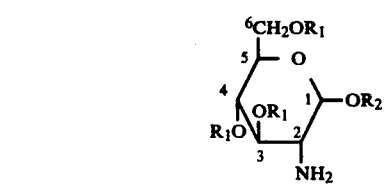

where:
$R_1$ = a hydrogen atom or an acetyl group,
$R_2$ = a hydrogen atom, an acetyl group, an aliphatic ($C_1$–$C_6$) group or a benzyl group
which is bonded by peptide linkage (—NHCO—) to an amino acid molecule or an oligopeptide molecule of:

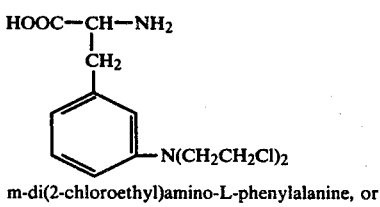

m-di(2-chloroethyl)amino-L-phenylalanine, or

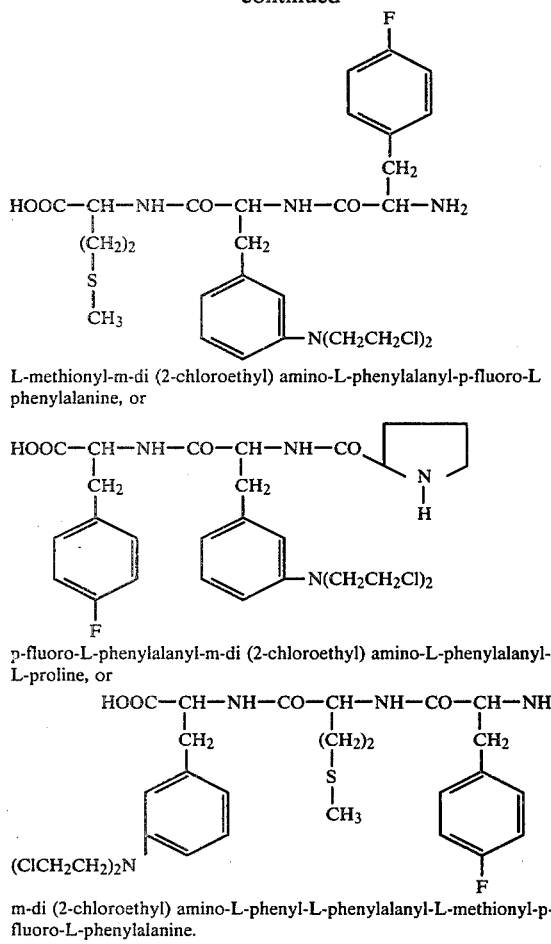

L-methionyl-m-di (2-chloroethyl) amino-L-phenylalanyl-p-fluoro-L-phenylalanine, or p-fluoro-L-phenylalanyl-m-di (2-chloroethyl) amino-L-phenylalanyl-L-proline, or m-di (2-chloroethyl) amino-L-phenyl-L-phenylalanyl-L-methionyl-p-fluoro-L-phenylalanine.

The peptide bond is between the amine group of the glucosamines of formula II and the terminal carboxylic acid group of the amino acid or oligopeptide. In every case, the amino acid or one of the amino acids in the oligopeptide in m-di(2-chloroethyl)amino-L-phenylalanine. The glucosamines of Formula II are carriers of the amino acids or oligopeptides.

It is in particular noted that, to have good antitumor activity against transplanted tumors in animals, all of the amino acids (including m-di(2-chloroethyl) amino-L-phenylalanine) used for the peptide synthesis and so forming the peptide moiety, must belong to the L-configuration. Among the compounds according to the present invention, the following are preferred:

(a) 1,3,4,6-tetra-O-acetyl-D-glucosamyl-m-di(2-chloroethyl)amino-L-phenylalanine

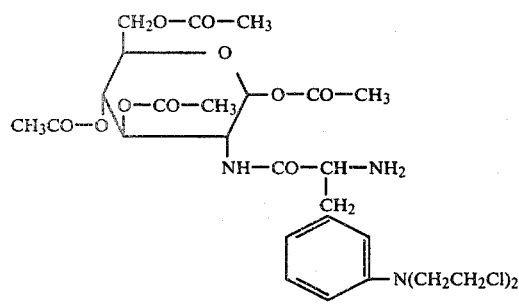

(b) D-ethyl-glucosamyl-m-di(2-chloroethyl)amino-L-phenylalanine hydrochloride

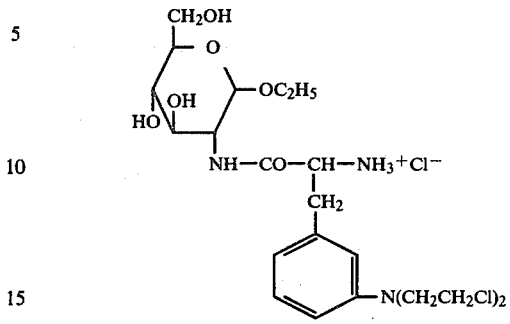

(c) 1,3,4,6-tetra-O-acetyl-D-glucosamyl-p-fluoro-L-phenylalanyl-m-di(2-chloroethyl)amino-L-phenylalanyl-L-proline,acetate
(d) D-ethyl-glucosamyl-p-fluoro-L-phenylanalyl-m-di(2-chloroethyl)amino-L-phenylalanyl-L-proline, hydrochloride
(e) D-glucosamyl-p-fluoro-L-phenylalanyl-m-di(2-chloroethyl)amino-L-phenylalanyl-L-proline, acetate
(f) D-ethyl-glucosamyl-m-di(2-chloroethyl)amino-L-phenylalanyl-L-methionyl-p-fluoro-L-phenylalanine, dihydrochloride
(g) 1,3,4,6-tetra-O-acetyl-glucosamyl-L-methionyl-m-di(2-chloroethyl)amino-L-phenylalanyl-p-fluoro-L-phenylalanine, hydrochloride
(h) D-glucosamyl-L-methionyl-m-di(2-chloroethyl)amino-p-fluoro-L-phenylalanine dihydrochloride
(i) D-methyl-glucosamyl-L-methionyl-m-di(2-chloroethyl)amino-L-phenylalanyl-p-fluoro-L-phenylalanine hydrochloride
(j) D-ethyl-glucosamyl-L-methionyl-m-di(2-chloroethyl)amino-L-phenylalanyl-p-fluoro-L-phenylalanine hydrochloride.

SYNTHESIS OF THE COMPOUNDS OF THE PRESENT INVENTION

The compounds of the present invention are prepared by protecting the terminal amino group of the amino acid or oligopeptide by acylation to form a Schiff base, as by reaction with carbobenzoxy chloride or formyl chloride. The thus acylated amino acid or thus acylated oligopeptide is reacted with a glucosamine of formula II in the presence of dicyclohexylcarbodiimide (DCC) whereby condensation to form the peptide linkage (—NHCO—) occurs. The terminal amino group is then deprotected by reagents which do not disturb peptide linkages. For example, deprotection may be achieved by catalytic hydrogenation with Pd/C and hydrogen gas or by hydrolysis with alcoholic hydrochloric acid. Use of the latter reagent also deacetylates the glucosamine derivative (at the $R_1$ and $R_2$ positions). See Examples 4 and 7 below.

D-glucosamine ($R_1 = R_2 =$ hydrogen atom in formula II) can be condensed directly with the amino acid or oligopeptide; that is, without passing through 1,3,4,6-tetra-O-acetyl-D-glucosamine. In other words, D-glucosamine is dissolved in a slightly aqueous alkaline solution and is reacted with the protected amino acid (e.g., formyl-amino acid) or protected oligopeptide (e.g. formylpeptide) dissolved in dimethylformamide (DMF) in the presence of DCC.

Other N-acyl derivatives of glucosamines of formula I (i.e. where both $R_1$ and $R_2$ are not a hydrogen atom) can be obtained by deacetylation of the respective derivatives of 1,3,4,6-tetra-O-D-glucosamine by means of alcoholic hydrochloric acid. See Examples 4, 7, and 8. The 1,3,4,6-tetra-O-acetyl-D-glucosamine ($R_1=R_2=$acetyl in formula II) reagent is synthesized from D-glucosamine by reaction of the latter with a protecting agent for the amino group (e.g. p-anisaldehyde) to form a Schiff's base. See Example 1(a). The Schiff's base is then acetylated with acetic anhydride (Example 1(b)), then hydrolized with hydrochloric acid (Example 1(c)) and treated with sodium acetate (for example) to obtain 1,3,4,6-tetra-O-acetyl-D-glucosamine. Examples 1(d) and 2(a). The resultant 1,3,4,6-tetra-O-acetyl-D-glucosamine is condensed with the acylated amino acid or oligopeptide in the presence of DCC as described above.

The peptide moiety of the N-acyl derivatives of the glucosamines of the present invention is synthesized according to methods already known. Synthesis of a dipeptide is by means of condensation via DCC between two amino acids blocked respectly at the amino group and the carboxyl group, followed by deprotection of the carboxyl group and condensation with the amino group of a third amino acid blocked at the carboxyl group by means of DCC. In this way an acylated peptide is obtained. For the purpose of selectively protecting the amino functional groups, the amino group is acylated, for example with formic acid or with carbobenzoxy chloride. The carboxyl groups are protected by means of esterification to the methyl, ethyl, hexyl or benzyl ester, which are then cleaved by cautious saponification.

The single compounds were analyzed and controlled by means of elemental analysis (chlorine-bonded, either with covalent or ionic bond—nitrogen, possibly sulphur), specific optical rotation, thin layer chromatography (silica gel G), UV spectrophotometry, IR spectrometry.

The chemotherapeutic activity was evaluated by means of two experimental models:

1. Determination of the MST (Mean Survival Time) of BDGI mice inoculated intraperitoneally with $10^6$ cells of lymphoid Leukemia L 1210 deriving from regular implants in DBA2 mice. The MST was determined both on the controls and on the animals treated, and thereafter an evaluation was made of the ILS (increased Life Span) according to Cancer Chemotherpy Reports 1972, Volume 3, No. 2 (Protocols for screening chemical agents and natural products against animal tumors and other biological systems—Third Edition, National Cancer Institute, Bethesda, Md.

In this case, the compounds were tested only after oral administration (as afterwards described), starting from the 4th day after implant of the tumor and continuing on the 8th, 12th and 16th day. On the 30th day, any surviving animals were sacrificed and the surviving animals were sacrificed and the experimient discontinued and evaluated. It should at this point be specified that whereas the first experiments on Sa. 180 (see following paragraph) were performed with injection of the products parenterally, the subsequent experiments were performed with administration of the products by the oral route—which, for other peptides not containing aminosugars, had given negative results. As has been stated it was surprisingly found that the peptides containing an aminosugar in their molecule are active by the oral route; and this is considered a great advance in antitumor chemotherapy, among other reasons, because of the greater ease of administration.

2. Inhibition of the growth of Sarcoma 180 according to the procedure established by CCNSC (Cancer Chemotherapy National Service Centre, U.S. Dept. of Health, Education and Welfare, Cancer Chemotherapy Reports, No. 25, Decemeber 1962).

This test was performed on Swiss albino carrying Sarcoma 180, transplanted every week; the sterility of the inoculum was in every case strictly controlled. Aqueous solutions or suspensions, stabilized with carboxymethyl cellulose, were administered intraperitoneally and/or orally on the 1st, 3rd, 5th, 7th day after implant of the tumor; the animals were sacrificed on the 9th day and determination made of tumor weight, percent variation of tumor weight as compared with the control tumors, WBC, spleen weight and carcass weight.

Chemotherapeutic research showed that all the compounds are active. In case of Sarcoma 180, the activity is thus seen to range from a minimum of 50% inhibition for certain of the compounds up to 94–96% for others. In this latter case, therefore, there is effective elimination of the tumor. Such a result demonstrates that the present invention achieves a substantial advance in experimental chemotherapy. Similar results were obtained with Leukemia L 1210, in which, taking Increased Life Span as a parameter of evaluation of the activity of a product, the values range from minima of 137 up to maxima of 263 and beyond—given that there are often animals surviving on the 30th day.

The antitumor chemotherapeutic activity of the compounds of the present invention are reported in an article by the inventor entitled "N-Acyl Derivatives of Glucosamine with Oligo-Peptides," *Current Chemotherapy*, Amer. Soc. of Microbiol., p. 1183 (April 1978). The article is herein incorporated by reference in its entirety. Tables 1 and 2, as reported in the article, show the antineoplasmic activity of the compounds of the present invention:

Table 1

Effect of N-acyl peptides of glucosamine, administered orally, on survival in tumor-bearing mice

| Compound | Doses in mg of m-SL/kg | MST* (days) | ILS** (days) | Survivors at 60th day*** |
|---|---|---|---|---|
| Leukemia L1210 | Controls | 10 | | |
| GlcN-p-FPhe-m-SL—Pro-acetate | 5.7 | 14 | 140 | 0/8 |
| | 8 | 14 | 140 | 0/8 |
| GlcN—Met-m-SL-p-FPbe | 5.7 | 15 | 150 | 0/8 |
| | 8 | 17.5 | 175 | 0/8 |
| Ec—GlcN—Met-m-SL-p-FPhe | 5.7 | 16 | 160 | 0/8 |
| | 8 | 20.5 | 205 | 0/8 |

Table 1-continued

Effect of N-acyl peptides of glucosamine, administered orally, on survival in tumor-bearing mice

| Compound | Doses in mg of m-SL/kg | MST* (days) | ILS** (days) | Survivors at 60th day*** |
|---|---|---|---|---|
| Me—GlcN—Met-m-SL-p-FPhe | 5.7 | 17 | 170 | 0/8 |
|  | 8 | 18 | 180 | 0/8 |
| Sarcoma 180 solid | Controls | 18 |  |  |
| GlcN-p-FPhe-m-SL—Pro-acetate | 5.7 | 18.5 | 103 | 0/8 |
|  | 8 | 14.5 | 80.5 | 0/8 |
| GlcN—Met-m-SL-p-FPhe | 5.7 | 28.5 | 158 | 1/8 |
|  | 8 | 33.5 | 186 | 0/8 |
| Et—GlcN—Met-m-SL-p-FPhe | 5.7 | 41.5 | 230.5 | 1/8 |
|  | 8 | 30 | 167 | 1/8 |
| Me—GlcN—Met-m-SL-p-FPhe | 5.7 | 34.5 | 192 | 2/8 |
|  | 8 | 33 | 183 | 1/8 |

*Mean survival time
**Increase in life span.
***Survivors were without tumor, i.e., cured animals.

Table 2

Effect of N-acyl peptides of glucosamine, administered orally, on sarcoma 180 solid

| Compound | % Variation of tumor wt. | | | | Deaths | |
|---|---|---|---|---|---|---|
|  | 4.1* | 5.7 | 5.7 i.p. | 8 | Orally | i.p. |
| 4Ac—GlcN-m-SL** |  |  |  | −6.92 | 0 |  |
| 4Ac—GlcN-p-FPhe-m-SL—Pro | −17.41 | −41.83 |  | −58.31 | 0 |  |
| GlcN-p-FPhe-m-SL—Pro-acetate | −22.66 | −58.89 | −70.36 | −67.21 | 0 | 0 |
| 4Ac—GlcN—Met-m-SL-p-FPhe | −34.23 | −57.18 |  | −72.40 | 0 |  |
| GlcN—Met-m-Sl-p-FPhe | −41.99 | −69.04 | −83.19 | −87.18 | 0 | 0 |
| Et—GlcN—Met-m-SL-p-FPhe | −54.18 | −80.24 | −82.98 | −91.17 | 0 | 8/12 |
| Et—GlcN-m-SL—Met-p-FPhe*** |  | −27.74 |  | −33.82 | 0 |  |
| Me—GlcN—Met-m-SL-p-FPhe | −68.22 | −84.2 | −88.65 | −90.12 | 0 | 2/12 |

*Dose in milligrams of m-SL contained in the compounds.
**At 16 mg/kg in m SL = −46.92.
***At 16 mg/kg in m-SL = −55.42.

In Tables 1 and 2 above, all amino acids in the N-acyl derivatives of the present invention are in the L-configuration. Additionally, M-SL is used as an abbreviation for m-di(2-chloroethyl) amino-L-phenylalanyl. GlcN is used as an abbreviation for glucosamyl.

Some examples illustrating the synthesis of some of the claimed compounds are listed hereunder. All temperatures are in °C. unless otherwise indicateed.

EXAMPLE 1

1,3,4,6-tetra-O-acetyl-D-glucosamyl-m-di-(2-chloroethyl)amino-L-phenylalanine (a)

N-(p-methoxy-benzylidene)-D-glucosamine(anisal-glucosamine) Intermediate I

To a solution of 215 g (1 M) of D (+) glucosamine.HCl in 1 liter of NaOH, 1N, 121.2 ml of p-anisaldehyde are added. The solid product precipitated is washed first with cold water and then with a mixture of ethanol and diethylether. It is then dried to yield 250 g (80% theoretical) of a white product: m.p.=165° C. (dec.) $[\alpha]_D^{20°} = +73.9°$ (c=1, acetic acid).

(b)

N-(p-methoxy-benzylidene)-1,3,4,6-tetra-O-acetyl-D-glucosamine. Intermediate II 750 ml of acetic anhydride are added to a cooled mixture of 250 mg of Intermediate I in 1250 ml of anhydrous pyridine at 5° C. The obtained solution is poured into an ice water mixture. The separated solid is filtered, washed first with water and then with petroleum ether whereby 365 g of product (m.p.=176°-180° C.) are obtained. By crystallization from absolute ethanol, 310 g of product (m.p.=180°-1° C.) are obtained.

(c) 1,3,4,6-tetra-O-acetyl-D-glucosamine. HCl Intermediate III 125 ml of 5N HCl are added to a boiling solution of 302 g of Intermediate II in 2 liters of acetone: the precipitation of the product takes place and is completed by additon of ether. The solid product is washed with ether to yield 245 g of white product: m.p.=230° C.; $[\alpha]_D^{20°} = +30.9°$ (c=1,H₂O).

(d)

Tetracetyl-D-glucosamine(1,3,4,6-tetra-O-acetyl-D-glucosamine). Intermediate IV 16.4 g of sodium acetate are added to a mixture of 38.4 g of intermediate III in 200 ml of water. The tetracetyl-D-glucosamine which is precipitated is extracted with chloroformic and the chloroformic extract is evaporated under vacuum. The solid residue is suspended in ether and filtered. 30.5 g of product (m.p.=127°-9° C.$[\alpha]_D^{20°} = +27.2°$ C. (c=1, chloroform)) is obtained.

(e)

N-(N-carbobenzoxy-m-di(2-chloroethyl)amino-L-phenylalanyl)1,3,4,6-tetra-O-acetyl-D-glucosamine. Intermediate V A solution of 17.4 g of intermediate IV, and 22 g of N-carbobenzoxy-m-di-(2-chloroethyl)amino-L-phenylalanine in 150 ml of chloroform at a temperature of 5° C., is added to a solution of 11.4 g of Dicyclohexylcarbodiimide in 50 ml of chloroform. Almost immediately the precipitation of the dicyclohexylurea takes place. The solid is removed by filtration and from the clear filtrate 34.5 g of solid are obtained by addition of 500 ml of ether. From ethyl acetate, 16 g of the product melting at 198°–9° C. are obtained. The product is chromatographically homogeneous and shows:

$[\alpha]_D^{20°} = -13.6$ (c=1, CHCl$_3$)
$[\alpha]_D^{20°} = +10.0°$ (c=1, acetic acid)

Analysis for C$_{35}$H$_{43}$Cl$_2$N$_3$O$_{12}$:

|   | % calculated | % found |
|---|---|---|
| N = | 5.46 | 5.46 |
| Cl = | 9.22 | 9.18 |

(f)
N-(m-di-(2-chloroethyl)amino-L-phenylalanyl)-1,3,4,6-tetra-O-acetyl-D-glucosamine To a mixture of 40 g of Intermediate V in 600 ml of methanol, and 8 ml of glacial acetic acid: 12 g of 5% Pd/C are added. Under vigorous stirring a stream of H$_2$ at room temperature is passed through the mixture for 6 hours. The suspension is warmed to 45° C. and filtered. The filtrate is evaporated under vacuum and the white residue is suspended in ether and filtered. 24 g of product melting at 153°–5° C. are obtained. The product is chromatographically homogeneous with $[\alpha]_D^{20°} = +24.9°$ (c=1,CHCl$_3$)

Analysis for C$_{27}$H$_{37}$Cl$_2$N$_3$O$_{10}$

|   | % calculated | % found |
|---|---|---|
| N | 6.62 | 6.59 |
| Cl | 11.17 | 11.12 |

EXAMPLE 2
1,3,4,6-tetra-O-acetyl-D-glucosamyl-p-fluoro-L-phenylalanyl-m-di-(2-chloroethyl)amino-L-phenylalanyl-N-carbobenzoxy-L-proline

(a)
1,3,4,6-tetra-O-acetyl-D-glucosamyl-p-fluoro-L-phenylalanyl-m-di-(2-chloroethyl)-amino-L-phenylalanyl-N-carbobenzoxy-L-proline 105.5 g of 1,3,4,6-tetra-O-acetyl-D-glucosamine chlorohydrate are dissolved in 600 ml of dimethylformamide (DMF). With stirring, 40 ml of triethylamine, then 175 g of N-carbobenzoxy-L-prolyl-m-di-(2-chloroethyl)amino-L-phenylalanyl-p-fluoro-phenylalanine and successively a 62 g solution of dicyclohexyl-carbodiimide in 50 ml of dimethylformamide are added to the DMF solution. Stirring is continued at room temperature overnight. The insoluble residue is then filtered off. The filtrate is diluted to 3 liters with ethylacetate. The organic phase is then washed with water. By concentration under vacuum and chilling a crystalline product is obtained which is filtered and washed with ether. The yield is 90 g.

The analysis for C$_{49}$H$_{58}$Cl$_2$FN$_5$O$_{14}$ gives:

|   | % calculated | % found |
|---|---|---|
| N = | 6.8 | 7.1 |
| Cl = | 6.9 | 7 |

$[\alpha]_D^{20°} = +30.87°$ (c=1,CH$_3$OH); $-50.12°$ (c=1,CHCl$_3$)

(b)
1,3,4,6-tetra-O-acetyl-D-glucosamyl-p-fluoro-L-phenyalanyl-m-di-(2-chloroethyl)amino-L-phenylalanyl-L-proline acetate 66 g of the product obtained in the preceeding step are dissolved in methanol and acetic acid and 30 g of 5% Pd/C are added. Then an H$_2$ stream under vigorous stirring at room temperature is passed through. The suspension is filtered and the filtrate evaporated under vacuum until almost dry. Then, by slowly adding ether and chilling, a white crop is formed. 46.5 g of 1,3,4,6-tetra-O-acetyl-D-glucosamyl-p-fluoro-L-phenylalanyl-m-di(2-chloroethyl)amino-L-phenylanyl-L-proline acetate are obtained (m.p. 148°–151° C.).

Analysis for C$_{43}$H$_{56}$Cl$_2$FN$_5$O$_{14}$ is:

|   | % calculated | % found |
|---|---|---|
| N = | 7.3 | 7.1 |
| Cl = | 7.2 | 6.98 |
| H$_2$O = | absent | absent |

$[\alpha]_D^{20°} = -14.4°$ (c=1,methanol)

EXAMPLE 3
D-glucosamyl-p-fluoro-L-phenylalanyl-m-di-(2-chloroethyl)amino-L-phenylalanyl-L-proline acetate 35 g of carbobenzoxy-L-prolyl-m-di-(2-chloroethyl)amino-L-phenylalanyl-p-fluoro-L-phenylalanine are dissolved in 250 ml of DMF. Then, 12 g of D-glucosamine hydrochloride dissolved in 40 ml of H$_2$O are added. To this solution, 4.2 g of NaHCO$_3$ are added. After cooling at 5° C., 15.5 g of dicyclohexylcarbodiimide dissolved in 20 ml of DMF are added to the solution. Filtration to eliminate the separated dicyclohexylurea is next, followed by pouring the decolorized filtrate under stirring into crushed ice. The solid which precipitates is filtered, washed first with water and then with petroleum ether, dried and crystallized from absolute ethanol. The yield is 138 g (m.p.=138°–142° C.).

Analysis for C$_{41}$H$_{50}$Cl$_2$FN$_5$O$_{10}$ is:

|   | % calculated | % found |
|---|---|---|
| N = | 8.1 | 7.9 |
| Cl = | 8.2 | 7.92 |

$[\alpha]_D^{20°} = +14.4°$ (c=1, methanol)

Removal of the carbobenzoxy protective group

To 9.5 g. of the previous compound add a 5 g suspension of 5% Pd/C in 300 ml of methanol and 10 ml of acetic acid. Continue stirring with passage of an H$_2$ stream therethrough. The suspension is then filtered, the filtrate is evaporated under vacuum, and the residue after suspension in ether gives 7.1 g of crystals melting at 104°–105° C.

Analysis for C$_{35}$H$_{48}$Cl$_2$FN$_5$O$_{10}$ is:

|   | % calculated | % found |
|---|---|---|
| N = | 8.9 | 8.7 |
| Cl = | 9.0 | 9.1 |

$[\alpha]_D^{20°} = +14.6°$ C. (c=1, acetic acid)

EXAMPLE 4

Ethyl-D-glucosamyl-p-fluoro-L-phenylalanyl-m-di-(2-chloroethyl)amino-L-phenylalanyl-L-proline, hydrochloride 20 g of the product obtained as per example no. 2 are dissolved in 100 ml of ethanolic solution 1.5 N HCl. The solution is kept at room temperature and protected from light until complete deacetylation is achieved. The solution is decolorized with carbon and is evaporated under vacuum. The dry residue is suspended in ether. The solid, crystallized from propyl alcohol, yields 8.5 g of product which melts at 140°–143° C.

Analysis for $C_{33}H_{45}Cl_3FN_5O_8$ is:

|  | % calculated | % found |
| --- | --- | --- |
| N = | 9.1 | 9.1 |
| Cl = | 13.9 | 14.1 |
| Cl ionic = | 4.6 | 5.2 |

EXAMPLE 5

1,3,4,6-tetra-O-acetyl-D-glucosamyl-L-methionyl-m-di(2-chloroethyl)amino-L-phenylalanyl-p-fluoro-L-phenylalanine hydrochloride

(a)

N-formyl-p-fluoro-L-phenylalanyl-m-di-(2-chloroethyl)amino-L-phenylalanyl-L-methionine ethyl ester 554 g of N-formyl-p-fluoro-L-phenylalanyl-m-di-(2-chloroethyl)amino-L-phenylalanine are dissolved in 4.5 liters of dimethyl formamide (DMF). The solution is heated slowly for the dissolution step and then cooled to 15° C. While stirring add: 172 g of N-hydroxysuccinimide + 225 g of dicyclohexylcarbodiimide + 1,235 g-moles of L-methionine ethyl-ester dissolved in DMF. After 16 hours of stirring at room temperature, the precipitated dicylcohexylurea is removed and to the stirred filtrate 18 liters of a mixture of water and ice are added. The white precipitate is filtered, washed with water and completely dried under vacuum. Yield: 710 g (97.2%); m.p. = 180°–182° C.; $[\alpha]_D^{20} = -7.0° \pm 1°$ (c=2, DMF).

| Analysis: | % calculated | % found |
| --- | --- | --- |
| S = | 4.86 | 4.84 |
| N = | 8.52 | 8.51 |
| Cl = | 10.78 | 10.72 |

(b)

N-formyl-p-fluoro-L-phenylalanyl-m-di(2-chloroethyl)amino-L-phenylalanyl-L-methionine.

100 g of ester obtained in (a) are dissolved in 600 ml of DMF around 40° C. The solution is left to cool to about room temperature. Then, over a period of ½ an hour a 170 ml NaOH 1 N aqueous solution is added. After 1 hour of stirring, the solution is neutralized by slowly adding 170 ml of 1N hydrochloric acid. The tripeptide acid starts to precipitate. After a few hours in a refrigerator the solid is filtered, washed with ether and dried to yield 90 g of product.

| Analysis: | % calculated | % found |
| --- | --- | --- |
| N (Kjeld.) = | 9.38 | 9.31 |
| Total Cl = | 11.87 | 11.82 |
| S = | 5.36 | 5.28 | m.p. = 150°–155° C.; $[\alpha]_D^{20} = -3°$ (c=1, DMF)
U.V. spectrum: $\epsilon_{257} = 16,169$
I.R. spectrum: complies with the intended structure.

(c)

1,3,4,6-tetra-O-acetyl-D-glucosamyl-m-di(2-chloroethyl)amino-L-phenylalanyl-N-formyl-p-fluoro-L-phenylalanine 10.5 g of peptide obtained as per step (b) are dissolved in 50 ml of DMF and to the solution thus obtained: 9.6 g of 1,3,4,6-tetra-O-acetyl-D-glucosamine hydrochloride and 2.5 g of triethylamine are added. To the cooled mixture 2.3 g of hydroxysuccinimide and 3.8 g dicyclohexylcarbodiimide in 24 ml of DMF are added. The mixture is stirred at room temperature for 3 days to complete the reaction. The product obtained is dissolved in ethyl acetate and the organic phase is washed with water. A compound precipitates which after purification shows: $[\alpha]_D^{20} = -15.4°$ (c=1, DMSO)

| Analysis: | Calculated | Found |
| --- | --- | --- |
| N % = | 7.30 | 7.30 |
| Cl % = | 7.50 | 7.40 |

I.R. spectrum complies with the intended structure.

(d)

1,3,4,6-tetra-O-acetyl-D-glucosamyl-L-methionyl-m-di-(2-chloroethyl)-amino-L-phenylalanyl-p-fluoro-L-phenylalamine.

10 g of the compound obtained in reaction (c) are dissolved in 60 ml of glacial acetic acid. While stirring, a stream of dry gaseous hydrochloric acid is passed through the solution up to saturation. The reaction mixture is then poured into 500 ml of ether kept under stirring. The white precipitate is washed with ether and dried yielding 9.2 g of product. The latter, after crystallization from isopropanol, gives a product with the following analytical figures:

|  | % calculated | % found |
| --- | --- | --- |
| N = | 7.24 | 7.27 |
| Cl ionic = | 3.66 | 3.56 |
| Total Cl = | 11.00 | 11.12 |
| $H_2O$ = |  | 1.7 | m.p. = 136°–9° C.; $[\alpha]_D^{20} = +40.4°$ (c=1, AcOH)
$\epsilon_{258} = 16,608$; $\epsilon_{302} = 2,447$
The IR spectrum complies with the intended structure.

EXAMPLE 6

Ethyl-D-glucosamyl-m-di-(2-chloroethyl)amino-L-phenylalanyl-L-methionyl-p-fluoro-L-phenylalanine

(a)

N-formyl-p-fluoro-L-phenylanyl-L-methionyl-m-di-(2-chloroethyl)amino-L-phenylalanine ethyl ester 98 g of N-formyl-p-fluoro-L-phenylalanyl-L-methionine dissolved in 565 ml of tetrahydrofurane are admixed with 0.287 moles of m-di-(2-chloroethyl)amino-L-phenylalanine ethyl ester. 63 g of dicyclohexylcarbodiimide are added. After stirring, the dicyclohexylurea is filtered out and the solvent is evaporated under vacuum to 1 liter. Then, about 4 liters of ether are added. 144 g of product (melting at 146°-154°) are obtianed. By further crystallization from 6000 ml of methanol, 100 g of white product melting at 155°-158° C. are obtained.

| Analysis: | % calculated | % found |
|---|---|---|
| N = | 8.52 | 8.90 |
| S = | 4.875 | 4.95 |
| Cl = | 10.78 | 10.76 |

$[\alpha]_D^{20°} = +11.8°$ (C=1, dioxane)

(b)
N-formyl-p-fluoro-L-phenylalanyl-L-methionyl-m-di-(2-chloroethyl)amino-L-phenylalanine 32 g of ester obtained in (a) are dissolved in 200 ml of DMSO. The solution is cooled and then 52 ml of NaOH 1 N at pH 11–12 is added. The solution is cooled and then neutralized to about pH 4 by slow addition of 52 ml of 1 N HCl. 400 ml of water is added to the neutralized solution. The white solid which separates is filtered, decolorized and crystallized from acetone. 19 g of product melting at 144°-147° C.

$[\alpha]_D^{20°} = +15.56$ (c=1,DMSO) are obtained.

| Analysis: | % calculated | % found |
|---|---|---|
| N (Kjeldhal) = | 8.90 | 8.82 |
| S = | 5.09 | 5.10 |
| Cl = | 11.26 | 11.16 |

(c)
1,3,4,6-tetra-O-acetyl-D-glucosamyl-m-di-(2-chloroethyl)amino-L-phenylalanyl-L-methionyl-N-formyl-p-fluoro-L-phenylalanine Dissolved in 600 ml of DMF are: 24.18 g of 1,3,4,6-tetra-O-acetyl-D-glucosamine hydrochloride, 9 ml of triethylamine+37.8 g of the peptide obtained from the previous reaction (b). The solution is filtered. Added to the filtrate is 13.6 g of dicyclohexylcarbodiimide. After stirring, the precipitated dicyclohexylurea is filtered out. To the filtrate are then added 1800 ml of chloroform, followed by extraction with water. From the organic phase, chloroform is evaporated and the product is precipitated from the resulting solution by addition of 900 ml of ether. After crystallization from methanol, 7.8 g of pure product are obtained melting at 206°-208° C.

| Analysis: | % calculated | % found |
|---|---|---|
| N (Dumas) = | 7.30 | 7.39 |
| S = | 3.34 | 3.38 |
| Cl = | 7.39 | 7.25 |

$[\alpha]_D^{20°} = +19°$ (c=1, DMSO)

(d)
Ethyl-D-glucosamyl-m-di-(2-chloroethyl)amino-L-phenylalanyl-L-methionyl-p-fluoro-L-phenylalanine 6.72 g of compound obtained as per the previous step (6c) are dissolved in 52.5 ml of 1 N HCl in absolute ethyl alcohol. The solution is stirred overnight, then filtered, followed by complete removal of the solvent under vacuum. The solid product is suspended in ethanol. 5.84 g of product are obtained, which decomposes at about 120° C.

| Analysis: | % calculated | % found |
|---|---|---|
| Total Cl = | 16.97 | 16.31 |
| Cl (ionic) = | 8.49 | 8.46 |
| S = | 3.84 | 3.88 |
| N = | 8.38 | 8.43 |

$[\alpha]_D^{20°} = +27.8°$ (c=1, EtOH 95°).

EXAMPLE 7

Ethyl-glucosamyl-L-methionyl-m-di-(2-chloroethyl)amino-L-phenylalanyl-p-fluoro-L-phenylalanine 11 g of 1,3,4,6-tetra-O-acetyl-D-glucosamyl-L-methionyl-m-di-(2-chloroethyl) amino-L-phenylalanyl-N-formyl-p-fluoro-L-phenylalanine (prepared according to example 5(c)) are suspended in 80 ml of 1.2 N HCl in ethanol. The mixture is kept stirred for 2 days at room temperature up to completion of the reaction. The reaction mixture is treated with charcoal, filtered and then poured into 400 ml of ether. A semi-solid mass is obtained which is washed with ether and then dissolved in warm ethanol. Upon cooling a precipitate is obtained. After drying, 6.5 g of product with m.p. 162°-4° C. (dec) results. Analysis for $C_{35}H_{50}Cl_2FN_5O_8S\cdot HCl$ is

|  | % calculated | % found |
|---|---|---|
| Total Cl | 12.84 | 12.63 |
| Cl ionic | 4.28 | 4.20 |
| N (Kjeld) | 8.46 | 8.42 |
| S total | 3.87 | 3.82 |
| H₂O at K.F. |  | 1.25 |

EXAMPLE 8

D-glucosamyl-L-methionyl-m-di-(2-chloroethyl)amino-L-phenylalanyl-p-fluoro-L-phenylalanine bihydrochloride 5 g of 1,3,4,6-tetra-O-acetyl-D-glucosamyl-L-methionil-m-di-(2-chloroethyl) amino-L-phenylalanyl-p-fluoro-phenylalanine (obtained as in example 5d) are dissolved in 45 ml of 25% ethanol, admixed with 5 ml of conc. HCl. The mixture is stirred for 48 hours, filtered with charcoal, and the filtrate is poured, drop by drop, into 150 ml of ether. 2 g of solid product are obtained in which glucosamine is in hemiacetalic form (as is confirmed by its capacity to reduce Fehling reagent). m.p.=98° C.

$[\alpha]_D^{20°}=25°$ (c=1, DMF). Analysis for $C_{33}H_{46}Cl_2FN_5O_8S_2HCl$ is:

|  | % calculated | % found |
|---|---|---|
| Total Cl | 16.97 | 16.89 |
| Cl ionic | 8.49 | 8.68 |
| N (Dumas) | 8.38 | 8.21 |
| S | 3.84 | 3.75 |
| H₂O at K.F. |  | 1.50 |

The theoretical values were calculated for the bihydrochloride. The hemiacetalic form is verified by the reducing capacity of the product against Fehling's reagent.

I claim:

1. A N-acyl derivative of glucosamine selected from the group consisting of a compound of the formula:

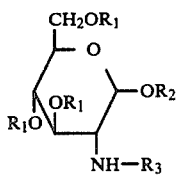

wherein:

R₁ is —H, —COCH₃;

R₂ is —H, —COCH₃, C₁ to C₆ alkyl, or a benzyl group;

R₃ is

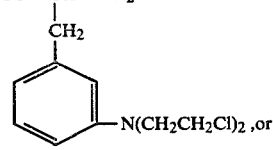

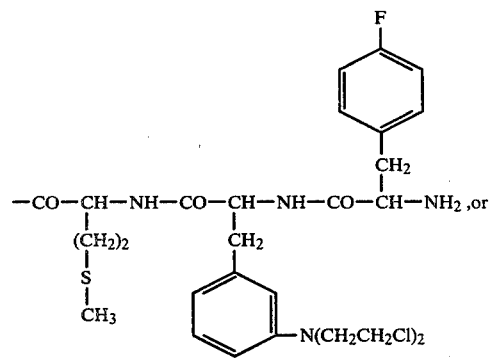

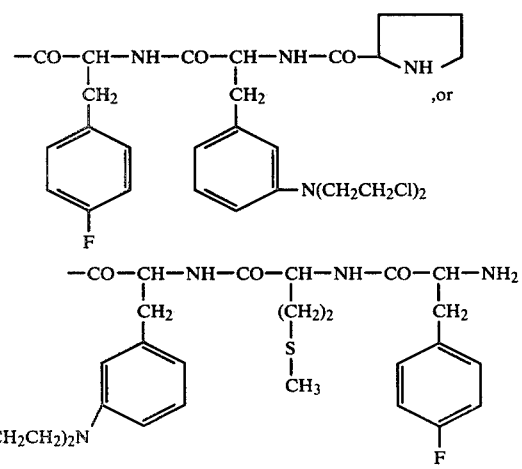

or a salt thereof with an organic or inorganic acid physiologically tolerated.

2. A N-acyl derivative as claimed in claim 1 selected from the group consisting of 1,3,4,6-tetra-O-acetyl-D-glucosamyl-m-di(2-chloroethyl)amino-L-phenylalanine and its salts with organic or inorganic acids physiologically tolerated.

3. A N-acyl derivative as claimed in claim 1 selected from the group consisting of D-ethyl-glucosamyl-m-di(2-chloroethyl)amino-L-phenylalanine and its salts with organic or inorganic acids physiologically tolerated.

4. A N-acyl derivative as claimed in claim 1 selected from the group consisting of 1,3,4,6-tetra-O-acetyl-D-glucosamyl-p-fluoro-L-phenylalanyl-m-di(2-chloroethyl) amino-L-phenylalanyl-L-proline and its salts with organic or inorganic acids physiologically tolerated.

5. A N-acyl derivative as claimed in claim 1 selected from the group consisting of D-ethyl-glucosamyl-p-fluoro-L-phenylalanyl-m-di(2-chloroethyl)amino-L-phenylalanyl-L-proline and its salts with organic or inorganic acids physiologically tolerated.

6. A N-acyl derivative as claimed in claim 1 selected from the group consisting of D-glucosamyl-p-fluoro-L-phenylalanyl-m-di(2-chloroethyl)amino-L-phenylanyl-L-proline and its salts with organic and inorganic acids physiologically tolerated.

7. A N-acyl derivative as claimed in claim 1 selected from the group consisting of D-ethyl-glucosamyl-m-di(2-chloroethyl)amino-L-phenylalanyl-L-methionyl-p-fluoro-L-phenylalanine and its salts with organic and inorganic acids physiologically tolerated.

8. A N-acyl derivative as claimed in claim 1 selected from the group consisting of 1,3,4,6-tetra-O-acetyl-D-glucosamyl-L-methionyl-m-di(2-chloroethyl)amino-L-phenylalanyl-p-fluoro-L-phenylalanine and its salts with organic or inorganic acids physiologically tolerated.

9. A N-acyl derivative according to claim 1 selected from the group consisting of D-glucosamyl-L-methionyl-m-di(chloroethyl)amino-L-phenylalanyl-p-fluoro-L-phenylalanine and its salts with organic and inorganic acids physiologically tolerated.

10. A N-acyl derivative according to claim 1 selected from the group consisting of D-methyl-glucosamyl-L-methionyl-m-di-(chloroethyl)amino-L-phenylalanyl-p-fluoro-L-phenylalanine and its salts with organic or inorganic acids physiologically tolerated.

11. A N-acyl derivative according to claim 1 selected from the group consisting of D-ethyl-glucosamyl-L-methionyl-m-di(2-chloroethyl)amino-L-phenylalanyl-p-fluoro-L-phenylalanine and its salts with organic or inorganic acids physiologically tolerated.

12. A N-acyl derivative according to claim 1 wherein R₂ is —H, —COCH₃, C₁ to C₆ alkyl, or benzyl.

13. A pharmaceutical composition which is effective in controlling transplanted neoplasms in animals comprising at least one N-acyl derivative of glucosamine as defined in any one of claims 1 through 12 as an active ingredient in a pharmaceutical carrier.

14. A method for chemotherapeutic treatment of a transplanted neoplastic disease in animals comprising administering a composition comprising at least one N-acyl derivative of glucosamine as defined in claim 1 as an active ingredient in a physiologically tolerable amount which is effective to control said neoplastic disease.

15. The method according to claim 14 wherein said composition is administered orally or parenterally.

16. The method according to claim 14 wherein said composition is administered in successive doses.

* * * * *